United States Patent
Wang

(10) Patent No.: US 6,503,648 B1
(45) Date of Patent: Jan. 7, 2003

(54) IMPLANTABLE FUEL CELL

(75) Inventor: Xingwu Wang, Wellsville, NY (US)

(73) Assignee: Biomed Solutions, LLC, West Henrietta, NY (US)

( * ) Notice: Subject to any disclaimer, the term of this patent is extended or adjusted under 35 U.S.C. 154(b) by 79 days.

(21) Appl. No.: 09/817,533

(22) Filed: Mar. 26, 2001

(51) Int. Cl.$^7$ ................................................ H01M 8/18
(52) U.S. Cl. ........................ 429/21; 429/7; 429/17; 429/19; 205/343; 205/628
(58) Field of Search .............................. 429/17, 19, 21, 429/7; 205/343, 628

(56) References Cited

U.S. PATENT DOCUMENTS

| | | |
|---|---|---|
| 3,837,922 A | 9/1974 | Ng |
| 4,087,976 A * | 5/1978 | Morrow et al. ........ 204/DIG. 4 |
| 4,294,891 A | 10/1981 | Yao |
| 4,490,232 A * | 12/1984 | Lapeyre ........................ 203/10 |
| 4,839,247 A * | 6/1989 | Levy et al. .................. 204/269 |
| 6,294,281 B1 * | 9/2001 | Heller ............................ 429/2 |

OTHER PUBLICATIONS

Radio Shack catalog, specification for part #273–1662; found on–line at http://support.radioshack.com//support_supplies/doc45/45509.htm.*

* cited by examiner

Primary Examiner—Carol Chaney
(74) Attorney, Agent, or Firm—Greenwald & Basch LLP; Howard J. Greenwald

(57) ABSTRACT

A fuel cell assembly comprised of an electrostrictive device for producing an electrical current, a device for producing a conditioned electrical current by conditioning the electrical current so that the amplitude of the electrical current does not vary by more than about 10 percent, an electrolytic device for converting water to hydrogen and oxygen with the conditioned electrical current, and a fuel cell device for converting the oxygen and hydrogen into a direct electrical current.

3 Claims, 4 Drawing Sheets

IMPLANTABLE FUEL CELL

FIELD OF THE INVENTION

A fuel cell assembly comprising an electrostrictive electromechanical power source and a fuel cell operatively connected to such source.

BACKGROUND OF THE INVENTION

Fuel cells are well known and are used for a variety of different purposes, including the production of power within a living organism.

Thus, by way of illustration, U.S. Pat. No. 3,837,922 issued in 1974 to Daniel Ng et al. This patent claimed a fuel cell adapted to be implanted in a body having an anode and an air-breathing cathode for producing electrical energy as derived from blood and air flowing through said fuel cell and supplying said electricity to a prosthetic device implanted in a human body. The fuel cell of this patent comprises: (a) a fuel cell housing adapted for implantation into said human body; (b) a first sinusoidal cell unit disposed in said housing comprising: i. a cathode assembly for receiving air comprising a catalytic cathode material applied to a support membrane, said support positioned in said housing to define a plurality of interconnected U-shaped cathode chambers said support having a relatively sinusoidal folded configuration and adapted to receive air in the interior of said U-shape; ii. said cathode support membrane being adapted to transfer ions between the anode and cathode; iii. a second membrane disposed in said housing positioned a spaced apart parallel distance from the sinusoidal cathode support to define an anolyte chamber therebetween; iv. an anode catalyst positioned in said anolyte chamber to define an anode; v. said second membrane adapted to separate a blood ultrafiltrate containing reactive organic compounds from whole blood and to transfer said reactive organic compounds into association with said anode; (c) a second sinusoidal cell unit disposed in said housing, of identical construction as the first cell unit, the second membrane of the second cell unit being positioned a parallel spaced apart distance from the second membrane of the first cell unit to define a blood chamber between said second membrane; (d) a conduit for transfer of air from the exterior of said body to said cathode chambers, said conduit adapted to be implanted in said body and having an opening communicating with the exterior of the body; (e) means for current collection from said anode and cathode to provide electrical current for said prosthetic device; f) means for connecting the first and second sinusoidal cell units electrically together in series or parallel, to provide a predetermined cell voltage and current output value range; (g) means for transfer of blood to said blood chamber; (h)said first cell and second cell positioned in said housing to provide blood and air flow through said blood chamber and cathode chamber. The entire disclosure of this United States patent, and of related U.S. Pat. No. 3,879,922, is hereby incorporated by reference into this specification.

By way of further illustration, in 1975 U.S. Pat. No. 3,861,397 issued to Raghavendra Rao et al. This patent claimed an implantable fuel cell, particularly for operating heart beat actuators, artificial hearts and the like, said cell in operational condition utilizing an oxidizable body substance, preferably glucose as fuel, and oxygen from the body fluids, said cell comprising an enclosure impermeable to body fluids, a fuel electrode means, at least one porous oxygen electrode means selectively reacting oxygen in the presence of fuel, said electrode means located in said enclosure and including associated electrical connection means for deriving electrical energy from the cell under the condition of operation, hydrophilic means which are non-permeable to proteinous substance, blood corpuscles, etc., spacing said electrode means from each other and said enclosure and means in said enclosure for guiding the diffusing operational mixture of fuel and oxygen first to said selective oxygen electrode means and there through to said fuel electrode means. The entire disclosure of each of these United States patents is hereby incorporated by reference into this specification.

By way of further illustration, in 1981 U.S. Pat. No. 4,294,891 issued to Shang J. Yao. This patent claimed a biologically acceptable, implantable, bio-oxidant fuel cell comprising in operative combination: (a) at least one anode assembly; (b) at least one cathode assembly; (c) a fuel/electrolyte chamber defined between said anode and said cathode assemblies for receiving an externally supplied fuel; (d) an electrical lead attached to each of said anode and cathode assembly to provide electrical output to a prosthesis; (e) a biologically acceptable, oxygen permeable membrane disposed substantially in contact with said cathode assembly so that said membrane lies between said cathode and body tissue, said membrane being adapted to permit endogenous tissue oxygen as a biological oxidant to diffuse into said cell from said body tissue; a (f) fuel/electrolyte composition disposed in said fuel/electrolyte chamber; and (g) said fuel/electrolyte composition having a high concentration ratio of fuel to endogenous tissue oxygen diffusing through said membrane into said cell. The entire disclosure of this United States patent is hereby incorporated by reference into this specification.

Thus, fuel cells which are implantable into a living organism have been known since at least as early as 1974. These prior art implantable fuel cells either utilized oxygen and hydrogen naturally present within the living organism and/or they produced some or all of the oxygen and/or hydrogen from electrolysis of bodily fluid. The prior art did not disclose effective means for powering the electrolysis reactions. Furthermore, the membrane technology used to separate the hydrogen and oxygen from each other was not well developed. Additionally, the fuel cell membrane, which also could be used to separate the oxygen and hydrogen from each other, was not effective.

In a book by Karl Kordesch et al., entitled "Fuel Cells and Their Applications" (VCH Verlagsgesellschaft mbH, Weinheim, Germany, 1996), it was disclosed at page 74 that "... progress in this technology was slow due to the 'drying out' of the membrane during operation of the system. The major problem with the General Electric fuel cell was keeping the membrane wet under operating conditions."

To the best of applicant's knowledge, the implantable fuel cells described in the patents discussed above never have been commercially available.

It is thus an object of this invention to provide a fuel cell assembly which durably and reliably produces electric power and which does not decline in performance with age.

SUMMARY OF THE INVENTION

In accordance with this invention, there is provided a fuel cell assembly comprised of a electrostrictive means for generating an electrical current, means for utilizing said electrical current to electrolyze water and produce oxygen and hydrogen, and fuel cell means for converting said oxygen and hydrogen into electrical energy.

BRIEF DESCRIPTION OF THE DRAWINGS

The invention will be described by reference to this specification and the enclosed drawings, in which like numerals refer to like elements, and wherein.

DESCRIPTION OF THE PREFERRED EMBODIMENTS

Figure 1:
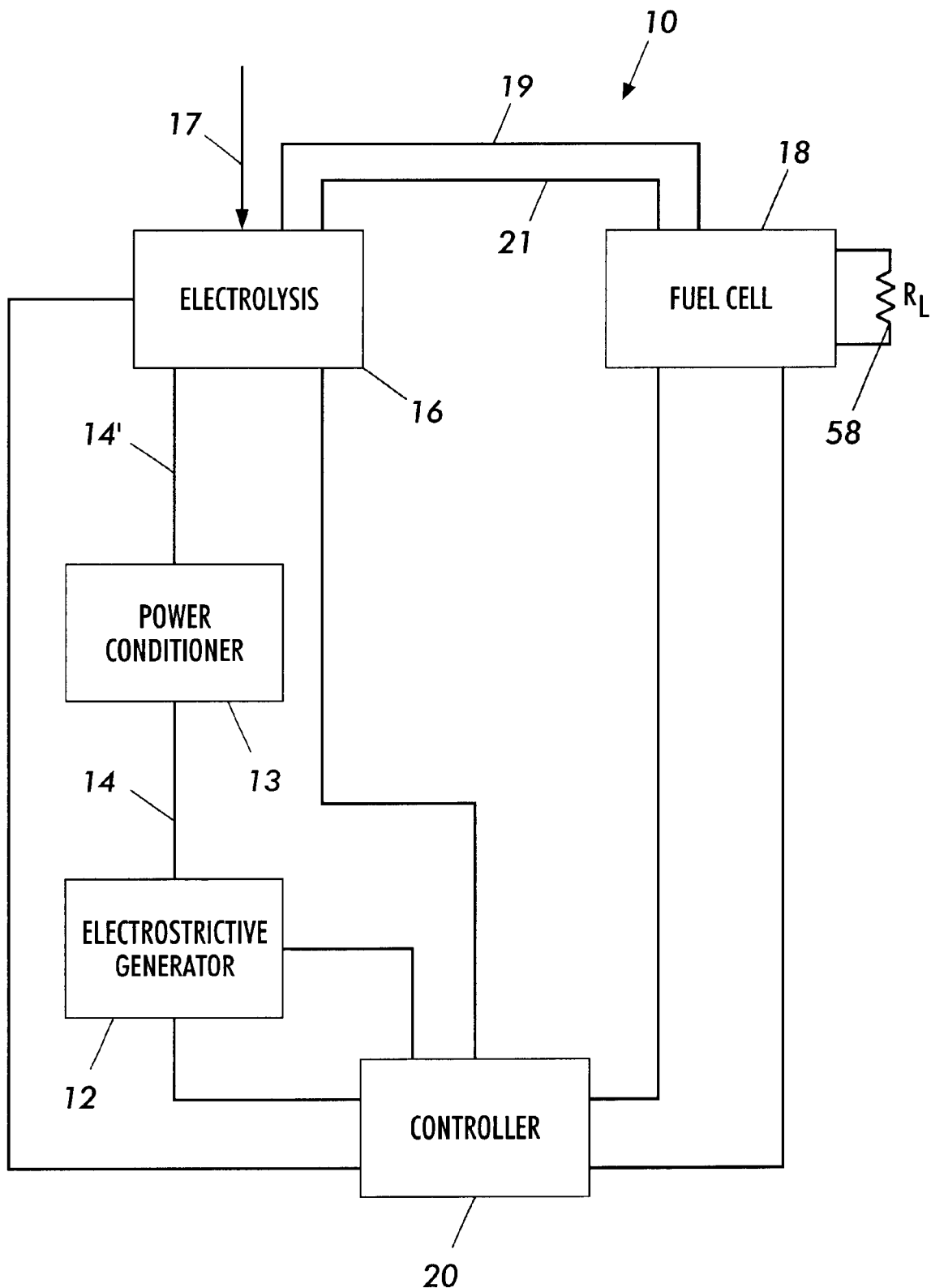
FIG. 1 is a schematic diagram of one preferred fuel cell assembly of the invention.

FIG. 1 is a schematic diagram of a fuel cell assembly 10. Referring to FIG. 1, an electrostrictive generator 12 is used to convert mechanical energy to electrical energy which thereafter is fed via line 14 to electrolysis unit 16, in which water is converted into hydrogen and oxygen for use in fuel cell 18.

The electrostrictive generator 10 utilizes an electrostrictive material. As used in this specification, an electrostrictive material is a relaxor ferroelectric material which exhibits a high dielectric constant (in excess of 20,000) and whose electric field output varies nonlinearly with the strain imposed upon the device. Thus, it differs from piezoelectric materials, whose electric field output varies linearly with strain.

Electrostrictive materials are more efficient than piezoelectric materials, producing an electric field both upon the imposition of the strain and its relaxation. They have been described in many United States patents.

By way of illustration, U.S. Pat. No. 6,093,667 of Keiji Kusumoto et al. discloses "Ceramics with excellent electrostrictive property" and claims a method of producing an electrostrictive solid solution ceramic, which comprises mixing lead oxide, nickel oxide, niobium oxide, and titanium oxide, forming the mixture into a body, heat treating the formed body in air, and next, dissolving unreacted product, separating particles of product, forming the particles, and then sintering the product in a lead oxide atmosphere to obtain the sintered body. The patentees discuss electrostrictive ceramics, which have recently received attention as ceramic actuator materials, and they refer to a text entitled "From Piezoelectric/Electrostrictive Actuator, Fundamentals to their Actual Use": Kenji Uchino, Morihoku Shuppani 1994). The entire disclosure of this United States patent is hereby incorporated by reference into this specification.

By way of further illustration, U.S. Pat. No. 6,091,182 discloses a piezoelectric/electrostrictive element By way of further illustration, reference may be had U.S. Pat. Nos. 5,862,002 (electrostrictive actuated mirror array), 5,814,920 (piezoelectrtic/electrostrictive element), 5,691,593 (piezoelectric/electrostrictive actuator), 5,684,243 (process for controlling sensitivity of electrostrictive transducers), 5,681,410 (piezoelectric/electrostrictive actuator), 5,631,040 (piezeoelectric/electrostrictive actuator), 5,622,748, 5,523,645 (electrostrictive effect element), 5,255,972, 5,210,455 (piezoelectric/electrostrictive actuator), 5,126,618 (laminar piezoelectric/electrostrictive driver), 5,126,615, 5,113,108 (hermetically sealed electrostrictive actuator), 5,032,558 (electrostrictive ceramic material), and the like. The entire disclosure of each of these United States patents is hereby incorporated by reference into this specification.

The electrostrictive generator 12 is comprised of either electrostrictive material, and/or both electorstrictive and piezoelectric material. In either event, the output of electrostrictive generator 12 is not linear with the strain applied or relaxed; and the electrostrictive generator 12 produces an output when strain is both applied and relaxed.

In one preferred embodiment, the electrical output from electrostrictive generator 12 is a direct current. The output from an electrostrictive element may be an alternating current. When such an a.c. current is produced by the altnerating straining and relaxation of the electrostrictive generator 12, the a.c. thus produced may be rectified to produce direct current by conventional rectification means. See, e.g., U.S. Pat. No. 4,756,290, the entire disclosure of which is hereby incorporated by reference into this specification.

It is preferred to condition the electrical output from the electrostrictive generator 12. As used in this specification, with regard to alternating current, the conditioned alternating current has a frequency and amplitude which do not vary more than 10 percent from one point in time to another. With regard to direct current, the amplitude of the direct current does not vary more than 10 percent from one point in time to another.

Thus, as is illustrated in the preferred embodiment depicted in FIG. 1, the electrical output from electrostrictive generator 12 may first be fed via line 14 to power conditioner 13 and, after being suitably conditioned and, optionally, rectified, then passed via line 14' to electrolysis unit 16.

One may use any of the power conditioning circuits known to those skilled in the art to regulate the amplitude of the power produced by generator 12. Thus, e.g., one may use one or more of the circuits disclosed in U.S. Pat. Nos. 6,166,458 (power conditioning unit), 6,075,350 (power line conditioner), 6,153,943 (power conditioning apparatus with energy conversion and storage), 6,118,251 (battery depassivation and conditioning method and apparatus), and the like. The entire disclosure of each of these United States patents is hereby incorporated by reference into this specification.

Referring again to FIG. 1, the direct current produced in electrostrictive generator 12 is fed via line 14 to electrolysis unit 16. Water is fed into such electrolysis unit 16 via line 17, hydrogen is removed from electrolysis unit 16 via line 19, and oxygen is removed from electrolysis unit 16 via line 21. Electrolytic devices for performing this function are well known. Thus, e.g., reference may be had to U.S. Pat. Nos. 6,063,258 (production of hydrogen from water using photocatalyst-electrolysis hybrid system), 5,795,666 (modular power station for the production of hydrogen), 4,957,610 (generation of hydrogen and oxygen), 4,3521,722 (integrated photovoltaic electrolytic cell), 4,225,401 (method for generating hydrogen and oxygen), 4,090,933 (photoelectrolysis of water by solar radiation), and the like. The entire disclosure of each of these United States patent is hereby incorporated by reference into this specification.

By way of illustration and not limitation, U.S. Pat. No. 4,225,401 discloses a method of generating hydrogen and oxygen by electrolytic decomposition of water in an electrolysis cell having an anode chamber and a cathode chamber provided with electrodes for applying a decomposition voltage, which method comprises in combination the steps of: adding to said cell an ionic moiety; introducing water to said cell; separating said anode and cathode chambers by an ion conducting material, applying an electrolysis current, and separately withdrawing hydrogen and oxygen from said cathode and anode chambers respectively. It will be readily apparent to those skilled in the art as to how the process of such patent can be utilized in applicant's invention. Many other patents describe similar devices.

Thus, by way of further illustration, the technology disclosed in U.S. Pat. No. 6,117,579 may be used to construct the electrolysis unit 16; the entire disclosure of U.S. Pat. No. 6,117,579 is hereby incorporated by reference into this specification. As will be apparent to those skilled in the art, a polymer electrolyte fuel cell (as disclosed in U.S. Pat. No. 6,117,579) may be used as an electrolysis cell merely by reversing the input and outputs. Instead of feeding oxygen and hydrogen to produce electricity, one may feed electricity to produce oxygen and hydrogen.

U.S. Pat. No. 6,117,579 describes and claims a polymer electrolyte fuel cell comprising: a plurality of assemblies, each assembly including a polymer electrolyte film with hydrogen ion conductivity and an electrode layer on opposite sides of said polymer electrolyte film thereby sandwiching said polymer electrolyte film therebetween; and a plurality of electrically conductive separators, each separator being piled alternatively with said assembly and including a gas supply channel to supply a gas to said electrode layer and a gas outlet channel for discharging a gas form said electrode layer, said electrode layer comprises at least one porous base area with water repellency and at least one penetration area higher in water permeability than in said base area wherein said electrode layer has non uniform water permeability throughout said electrode.

Because the functions of electrolysis unit 16 and fuel cell unit 18 are reversible, one can produce one unit (not shown) which will, in response to a signal from controller 20, either produce hydrogen and oxygen from water, or produce electricity from hydrogen and oxygen. When the combined device has only one set of electrodes, only one of these functions can be performed at any one time. However, when the combined device has two sets of electrodes within one hermetic enclosure, both functions can be performed simultaneously.

Figure 2:
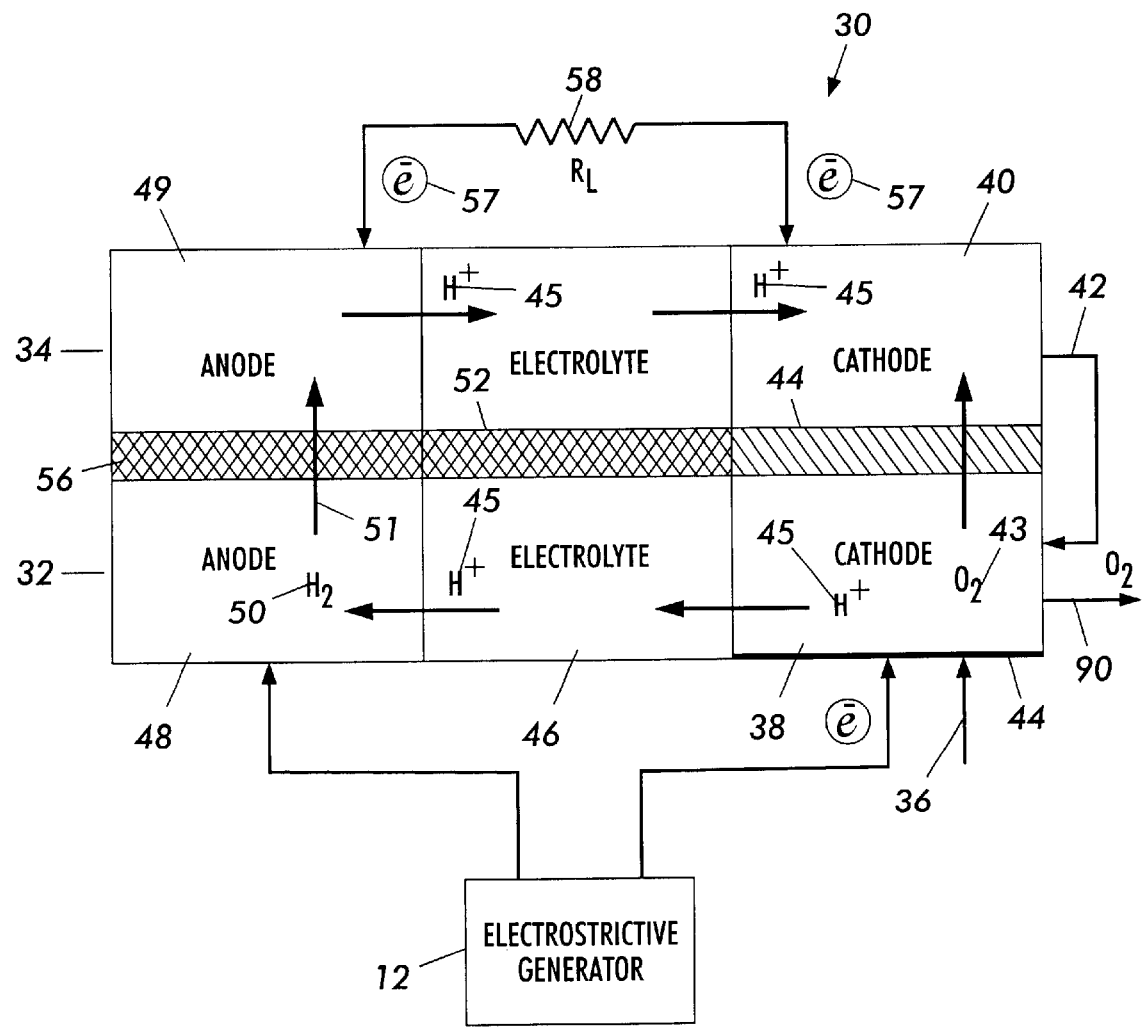
FIG. 2 is a schematic diagram of one preferred electrolytic means for extracting hydrogen and oxygen from water and producing electricity from such hydrogen and oxygen.

FIG. 2 is a schematic of one such combined device 30 which may be used in applicant's invention. Referring to FIG. 2, it will be seen that device 30 comprises twin cells 32 and 34.

Cell 32 produces oxygen and hydrogen from water. Water is fed into cell 32 via line 36. Alternatively, or additionally, water may be fed into the cathode 38 of cell 32 from cathode 40 of cell 34, via line 42.

In one embodiment, twin cell assembly 30 is implanted within a living body and the water fed via line 36 is water in the living organism which flows a permeable membrane 44. Membranes which are permeable to water are well known and are described in, e.g., U.S. Pat. Nos. 6,106,964, 6,063,278, 6,045,934, 5,996,976, 5,965,288, 5,820,574, and the like. The entire disclosure of each of these United States patents is hereby incorporated by reference into this specification.

Referring again to FIG. 2, the water which is fed through "line 36" (and/or which permeates through the membrane 44) is converted into oxygen in cathode 38; and the oxygen 43 then diffuses through oxygen permeable membrane 44 into cathode 40. One may use any of the oxygen permeable membranes 44 known to those skilled in the art. Reference may be had, e.g., to U.S. Pat. Nos. 5,674,270 (thermal pad having a common attachment and oxygen permeable site), 6,077,323 (synthesis gas production by ion transport membranes), 5,374,243 (oxygen permeable bag containing oxygen-transporting perfluorochemical for providing oxygen internally to mammals), 5,229,465 (oxygen permeable polymeric membranes), 5,177,167 (oxygen permeable shaped articles), 5,147,424 (oxygen permeable polymeric membranes), 5,039,404 (oxygen permeable membrane used in wastewater treatment), and the like. The entire disclosure of each of these United States patents is hereby incorporated by reference into this specification.

Referring again to FIG. 2, when oxygen permeates across oxygen permeable membrane 44, hydrogen ion 45 permeates into electrolyte 46 and thence to anode 48, wherein it is converted to hydrogen 50. This process is the well known electrolysis process described in the patents discussed elsewhere in this specification.

There is a barrier 52 between electrolyte 46 and electrolyte 54. Nothing permeates through barrier 52, not hydrogen, not oxygen, not hydrogen ion. This barrier may be constructed for imperemable, nonconductive material such as, e.g., stainless steel, aluminum nitride, and the like.

By comparison, there is a hydrogen permeable membrane 56 disposed between anode 48 and anode 49 which allows hydrogen to flow in the direction of arrow 51. One may use any of the hydrogen permeable membranes known to those skilled in the art. Reference may be had, e.g., to U.S. Pat. Nos. 6,168,542, 6,171,574, 6,152,995, 5,227,141, 4,793, 829, 4,699,637, 4,654,047, 4,589,891, 4,394,294, and the like The entire disclosure of each of these United States patents is hereby incorporated by reference into this specification.

Referring again to FIG. 2, after the hydrogen gas diffuses into anode 49, an electron 56 is caused to flow through the load 58 and thence back to cathode 40. Simultaneously, hydrogen ion 45 diffuses into electrolyte 54 and through such electrolyte into cathode 40. The hydrogen ion 45 ad the oxygen 43 within the cathode 40 combine with the electron 56 to produce water, which is recycled via line 42 to cathode 38.

The assembly 30, with or without the electrostrictive generator 12, can be disposed within a biocompatible enclosure (not shown), and the entire biocompatible enclosure may be implanted within a living organism. The system thus described takes nothing from the living organism but water, which is in plentiful supply; and it supplies nothing to the living organism except electricity, which can be used to power other implantable devices, such as a pacemaker, etc.

One may use any of the implantable biocompatible enclosures known to those skilled in the art. Reference maybe had, e.g., to U.S. Pat. Nos. 6,068,651, 6,018,681, 6,006,132, 5,999,851, 5,807,397, 5,676,153, 5,674,249, 5,662,711, 5,605,159, 5,601,609, 5,591,217, 5,554,175, 5,549,646, and the like. The entire disclosure of each of these United States patents is hereby incorporated by reference into this specification.

Referring again to FIG. 2, the electrostrictive generator may be disposed outside of a living organism, or it may be disposed inside of such organism in such a location that it periodically is stressed and relaxed with the required degree of force.

Figure 3:
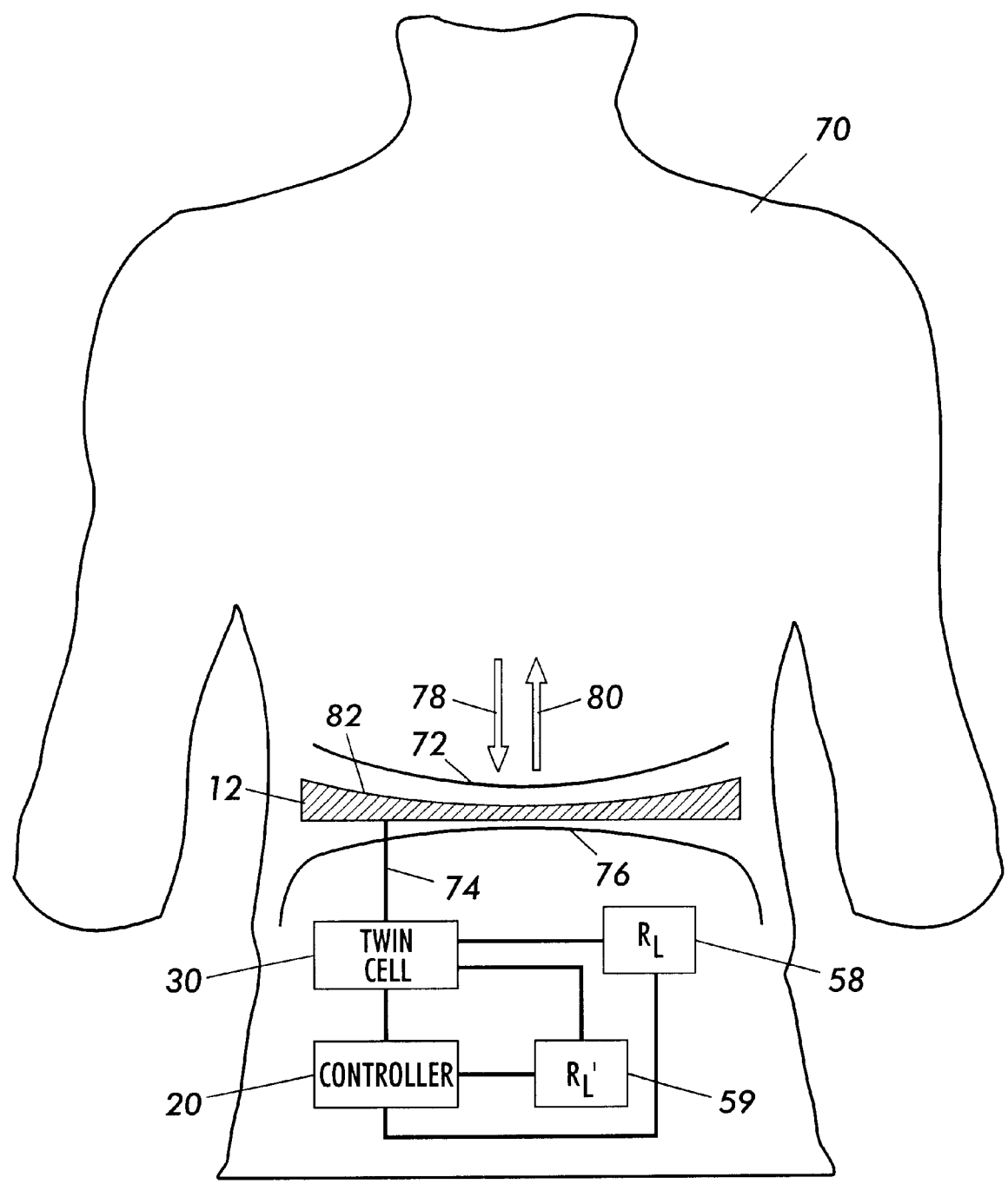
FIG. 3 is a schematic diagram of an implantable fuel cell assembly within a living organism.

FIG. 3 schematically illustrates one preferred embodiment in which an electrostrictive generator is disposed within a human body. Referring to FIG. 3, and to the preferred embodiment depicted therein, a patient 70 has disposed within his body, beneath his diaphragm 72, a formed article 12 consisting of electrostrictive material which is electrically connected via line 74 to twin electrolytic cell device 30 (see FIG. 2). The electrostrictive generator is disposed between the diaphragm 72 and the abdominal wall 76.

As the diaphragm 72 moves in the direction of arrow 78, it compresses the electrostrictive generator 12 between such diaphragm and the abdominal wall 76, thereby subjecting it to strain and causing it to produce electrical current. Thereafter, as the diaphragm relaxes and moves in the direction of arrow 80, the strain imposed upon electrostrictive generator 12 is relaxed, and such relaxation causes another pulse of electricity to flow from such generator.

The electricity thus produced is then fed to twin electrolytic cell assembly 30, which preferably is enclosed within a hermetic enclosure and contains a rectification circuit (not shown) to convert the alternating current to direct current. Thereafter, after such rectification, the twin cell device 30 produces hydrogen and oxygen in situ, consumes such hydrogen and oxygen to produce electricity, produces water which is then reused, and produces power which is fed to implantable device 82.

In the preferred embodiment depicted in FIG. 2, a multiplicity of different implantable devices 58, 59 et seq. may be powered by the twin cell assembly 30. These devices may be, e.g., a pacemaker, an implantable cytometer, an artificial organ, etc.; and their operation is preferably coordinated by controller 20.

By way of further illustration, the device 30 may be used to power a system of implantable devices for monitoring and/or affecting body parameters. Such as system is disclosed in U.S. Pat. No. 6,164,284, the entire disclosure of which is hereby incorporated by reference into this specification. This patent discloses a system for monitoring and/or affecting parameters of a patient's body and more particularly to such a system comprised of a system control unit (SCU) and one or more other devices, preferably battery-powered, implanted in the patient's body, i.e., within the envelope defined by the patient's skin. Each such implanted en f device is configured to be monitored and/or controlled by the SCU via a wireless communication channel. The SCU comprises a programmable unit capable of (1) transmitting commands to at least some of a plurality of implanted devices and (2) receiving data signal from at least some of those implanted devices. In one embodiment, the system operates in closed loop fashion whereby the commands transmitted by the SCU are dependent, in part, on the content of the data signals received by the SCU. A preferred SCU is similarly implemented as a device capable of being implanted beneath a patient's skin, preferably having an axial dimension of less than 60 mm and a lateral dimension of less than 6 mm. Wireless communication between the SCU and the implanted devices is preferably implemented via a modulated sound signal, AC magnetic field, RF signal, or electric conduction.

Referring again to FIG. 3, the electrostrictive generator 12 may be enclosed with a deformable and elastic casing 82. When casing 82 is compressed between diaphragm 72 and abdominal wall 76, it will impose strain upon the electrostrictive generator 12 while simultaneously protecting electrostrictive generator 12 from endogenous fluid. In one embodiment, the casing 82 is made from a flexible, elastic biocompatible material.

Although the electrostrictive generator 12 is shown disposed beneath the patient's diaphragm 72, it will be apparent that such generator 12 may be disposed beneath or nearby other parts of a body which expand and contract. Thus, by way of illustration and not limitation, the generator 12 may be positioned between lung and ribcage, between muscle and bone, between a heart and a sternum, and the like. In one embodiment, the generator 12 is implanted within a patient's foot, or in the palm of a patient's hand, or within a patient's hip joint.

Regardless of where the electrostrictive generator 12 is disposed, every time it is actuated by mechanical force, it will produce electricity which, in turn, will ultimately produce oxygen and hydrogen. This oxygen and hydrogen will be produced within twin cell 30 which will utilize such gases, as needed, to power the loads to which twin cell 30 is connected. To the extent that such gases are produced but not immediately used by twin cell 30, they may be stored within a reservoir within such cell (not shown) until they are used.

In one embodiment, and referring to FIG. 2, excess oxygen produced by device 30 may be fed via line 90 to any organ within the patient's body wherein such oxygen might be advantageously utilized.

In one embodiment, and again referring to FIG. 2, the electrolyte 54 is an electrolyte membrane which, preferably, is a polymer membrane. These fuel cell polymer membranes are well known. See, e.g., U.S. Pat. Nos. 6,103,414, 6,074, 692, 6,059,943, 6,042,958, 6,020,083, 6,011,500, 5,989,742, 5,879,828, 5,654,109, 5,599,638, 5,525,436, 5,498,639, 5,422,411, 5,318,863, and the like. The entire disclosure of each of these United States patents is hereby incorporated by reference into this specification.

Figure 4:
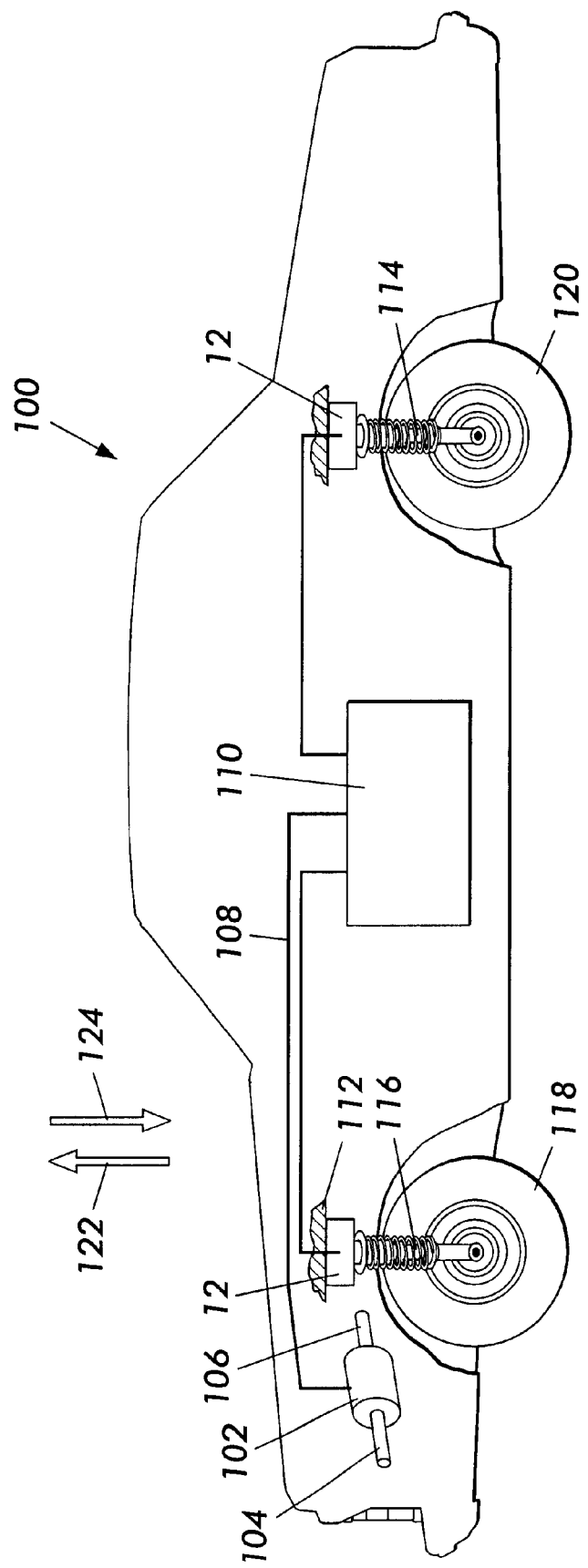
FIG. 4 is a schematic diagram of a fuel cell assembly incorporated into a motor vehicle.

FIG. 4 is a schematic diagram of an electric car 100 in which an electric motor is operatively connected via shafts 104 and 106 to a transmission (not shown). The electric motor 106 is electrically connected via line 108 to fuel cell device 110. Electrical power is furnished to fuel cell device 110 by electrostrictive generators 12 which are mounted onto the chasis 112 of the car 100, preferably above springs 114 and 116. As will be apparent, when car 100 is in motion, the wheels 118 and 120 will bounce up and down in the direction of arrows 122 and 124 and repeatedly impose strain upon generators 12 and thereafter release such strain. Such motions, and the forces they involve, will produce a steady stream of electrical current from the generators. The current may be rectified by conventional means before being fed to fuel cell 110.

Other means of imposing and releasing strain upon generators 12 also may be used. Thus, e.g., a windmill mounted on car 100 can repeatedly impose and release strain upon such generators 12.

In another embodiment, not shown, a portable CD player mounted upon an exerciser's body can be powered by electrostrictive generators 12 as the exerciser moves and as the CD player repeatedly is bounced against such exerciser's body.

In another embodiment, a electrostrictive generator can be adapted to fit within the hand of a user who, by repeatedly compressing it and releasing the compression force, can continually generate electricity.

In yet another embodiment, an electrostrictive generator can be disposed within a roadway and, as cars travel over a portion of such roadway and repeatedly compress and relax such electrostrictive generator, power can be furnished to a twin cell 30 which, in turn, can be used to power lamps, road signs, etc.

Hand-powered radios which produce electricity from the compression of a internal spring (which is used to power a generator) may be replaced by a similar radio in which an electrostrictive generator 12 is compressed rather than a spring.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A fuel cell assembly comprised of an electrostrictive means for producing an electrical current, means for producing a conditioned electrical current by conditioning said electrical current so that the amplitude of said electrical current does not vary by more than about 10 percent, electrolytic means for converting water to hydrogen and oxygen with said conditioned electrical current, and a fuel cell means for converting said oxygen and hydrogen into a direct electrical current.

2. The fuel cell assembly as recited in claim 1, wherein said electrolytic means is an implantable electrolytic means.

3. The fuel cell assembly as recited in claim 2, wherein said fuel cell means is an implantable fuel cell means.

* * * * *